(12) United States Patent
Gonzales et al.

(10) Patent No.: US 10,786,383 B2
(45) Date of Patent: Sep. 29, 2020

(54) APPARATUS AND METHODS FOR CORRECTING NASAL VALVE COLLAPSE

(71) Applicant: Spirox, Inc., Redwood City, CA (US)

(72) Inventors: Donald A. Gonzales, Austin, TX (US); Christopher M. Revell, San Antonio, TX (US)

(73) Assignee: Spirox, Inc., Redwood City, CA (US)

( * ) Notice: Subject to any disclaimer, the term of this patent is extended or adjusted under 35 U.S.C. 154(b) by 186 days.

(21) Appl. No.: 15/423,345

(22) Filed: Feb. 2, 2017

(65) Prior Publication Data

US 2017/0143532 A1    May 25, 2017

Related U.S. Application Data

(63) Continuation of application No. 13/129,846, filed as application No. PCT/US2009/064689 on Nov. 17, 2009, now Pat. No. 9,597,220.

(Continued)

(51) Int. Cl.
*A61F 5/08* (2006.01)
*A61B 17/064* (2006.01)
(Continued)

(52) U.S. Cl.
CPC ............. *A61F 5/08* (2013.01); *A61B 17/064* (2013.01); *A61B 17/0642* (2013.01);
(Continued)

(58) Field of Classification Search
CPC .......... A61F 5/08; A61F 2/186; A61B 17/064; A61B 17/0642
See application file for complete search history.

(56) References Cited

U.S. PATENT DOCUMENTS 2,173,848 A    9/1939   Kraus
3,395,709 A    8/1968   Rubin
(Continued)

FOREIGN PATENT DOCUMENTS

EP    1216013 B1    6/2006
EP    1857078 A     11/2007
(Continued)

OTHER PUBLICATIONS

Parylene Engineering; Why use parylene; retrieved from the internet (http://www.paryleneengineering.com/why_use_parylene.htm); 3 pages; on Oct. 2, 2017.
Friedman et al.; A simplified technique for airway correction at the nasal valve area; Otolaryngol Head Neck Surg; 131(4); pp. 519-524; Oct. 2004.
Kalan et al.; Treatment of external nasal valve (alar rim) collapse with an alar strut; Journal of Laryngology and Otology; 115(10); pp. 788-791; Oct. 2001.
(Continued)

*Primary Examiner* — Richard G Louis
(74) *Attorney, Agent, or Firm* — McDonnell Boehnen Hulbert & Berghoff LLP (57) ABSTRACT

The present invention relates to apparatus and methods for correcting nasal valve collapse comprising a device configured for suspending a nasal valve, the device comprising a body portion comprising a proximal end, a distal end, and a plurality of barbs, wherein the body portion is configured to be inserted through or underneath the upper lateral cartilage of a patient and wherein the plurality of barbs are configured to engage a soft tissue overlying a bony tissue proximal to the upper lateral cartilage, and a head portion coupled to the proximal end of the body portion wherein the head portion is configured to engage the upper lateral cartilage of the patient when the plurality of barbs are engaged with the soft tissue overlying the bony tissue proximal to the upper lateral cartilage.

18 Claims, 4 Drawing Sheets

Related U.S. Application Data (60) Provisional application No. 61/116,112, filed on Nov. 19, 2008.

(51) Int. Cl.
*A61F 2/18* (2006.01)
*A61B 17/00* (2006.01)

(52) U.S. Cl.
CPC .... *A61F 2/186* (2013.01); *A61B 2017/00004* (2013.01); *A61B 2017/0646* (2013.01); *A61B 2017/0647* (2013.01)

(56) References Cited

U.S. PATENT DOCUMENTS

| | | | |
|---|---|---|---|
| 3,716,058 A | 2/1973 | Tanner, Jr. | |
| 4,265,246 A | 5/1981 | Barry | |
| 4,461,281 A | 7/1984 | Carson | |
| 4,645,491 A | 2/1987 | Evans | |
| 4,938,234 A | 7/1990 | Capriotti | |
| 5,131,382 A | 7/1992 | Meyer | |
| 5,163,952 A | 11/1992 | Froix | |
| 5,261,916 A | 11/1993 | Engelson | |
| 5,286,254 A | 2/1994 | Shapland et al. | |
| 5,342,348 A | 8/1994 | Kaplan | |
| 5,356,431 A | 10/1994 | Pierce | |
| 5,358,522 A | 10/1994 | Montgomery et al. | |
| 5,411,550 A | 5/1995 | Hetweck et al. | |
| 5,419,760 A | 5/1995 | Narciso | |
| 5,464,450 A | 11/1995 | Buscemi et al. | |
| 5,500,013 A | 3/1996 | Buscemi et al. | |
| 5,531,744 A | 7/1996 | Nardella et al. | |
| 5,533,440 A | 7/1996 | Sher | |
| 5,545,208 A | 8/1996 | Wolff et al. | |
| 5,551,954 A | 9/1996 | Buscemi et al. | |
| 5,591,227 A | 1/1997 | Dinh et al. | |
| 5,634,926 A * | 6/1997 | Jobe | A61B 17/0401 606/281 |
| 5,637,113 A | 6/1997 | Tartaglia et al. | |
| 5,649,977 A | 7/1997 | Campbell | |
| 5,679,400 A | 10/1997 | Tuch | |
| 5,683,448 A | 11/1997 | Cragg | |
| 5,730,744 A | 3/1998 | Justin et al. | |
| 5,735,811 A | 4/1998 | Brisken | |
| 5,749,893 A | 5/1998 | Vidal et al. | |
| 5,766,237 A | 6/1998 | Cragg | |
| 5,769,883 A | 6/1998 | Buscemi et al. | |
| 5,785,647 A | 7/1998 | Tompkins et al. | |
| 5,837,008 A | 11/1998 | Berg et al. | |
| 5,843,084 A * | 12/1998 | Hart | A61B 17/064 606/77 |
| 5,843,172 A | 12/1998 | Yan | |
| 5,891,108 A | 4/1999 | Leone et al. | |
| 5,893,840 A | 4/1999 | Hull et al. | |
| 5,897,523 A | 4/1999 | Wright et al. | |
| 5,951,586 A | 9/1999 | Berg et al. | |
| 5,972,027 A | 10/1999 | Johnson | |
| 5,980,551 A | 11/1999 | Summers et al. | |
| 5,980,564 A | 11/1999 | Stinson | |
| 5,980,566 A | 11/1999 | Alt et al. | |
| 6,010,054 A | 1/2000 | Johnson et al. | |
| 6,063,101 A | 5/2000 | Jacobsen et al. | |
| 6,071,305 A | 6/2000 | Brown et al. | |
| 6,099,561 A | 8/2000 | Alt | |
| 6,106,541 A | 8/2000 | Hurbis | |
| 6,165,210 A | 12/2000 | Lau et al. | |
| 6,183,433 B1 | 2/2001 | Bays | |
| 6,238,411 B1 | 5/2001 | Thorner | |
| 6,241,747 B1 | 6/2001 | Ruff | |
| 6,241,762 B1 | 6/2001 | Shanley | |
| 6,250,307 B1 | 6/2001 | Conrad et al. | |
| 6,268,405 B1 | 7/2001 | Yao et al. | |
| 6,290,673 B1 | 9/2001 | Shanley | |
| 6,293,967 B1 | 9/2001 | Shanley | |
| 6,296,641 B2 * | 10/2001 | Burkhead | A61F 2/0811 606/213 |
| 6,322,590 B1 | 11/2001 | Sillers et al. | |
| 6,390,096 B1 | 5/2002 | Conrad et al. | |
| 6,401,717 B1 | 6/2002 | Conrad et al. | |
| 6,415,796 B1 | 7/2002 | Conrad et al. | |
| 6,431,174 B1 | 8/2002 | Knudson et al. | |
| 6,450,169 B1 | 9/2002 | Conrad et al. | |
| 6,454,803 B1 | 9/2002 | Romo | |
| 6,516,806 B2 | 2/2003 | Knudson et al. | |
| 6,656,195 B2 | 12/2003 | Peters et al. | |
| 6,878,165 B2 | 4/2005 | Makino | |
| 6,899,105 B2 | 5/2005 | Krueger et al. | |
| 6,978,781 B1 | 12/2005 | Jordan | |
| 6,982,359 B1 | 1/2006 | Beaudry | |
| 7,055,523 B1 | 6/2006 | Brown | |
| 7,114,495 B2 | 10/2006 | Lockwood | |
| D536,792 S | 2/2007 | Krueger et al. | |
| 7,213,599 B2 | 5/2007 | Conrad et al. | |
| 7,237,554 B2 | 7/2007 | Conrad et al. | |
| 7,322,356 B2 | 1/2008 | Critzer et al. | |
| 7,322,993 B2 | 1/2008 | Metzger et al. | |
| 7,337,781 B2 | 3/2008 | Vassallo | |
| 7,381,222 B2 | 6/2008 | Pflueger et al. | |
| 7,396,232 B2 | 7/2008 | Fromovich et al. | |
| 7,419,497 B2 | 9/2008 | Muni et al. | |
| 7,563,267 B2 | 7/2009 | Goldfarb et al. | |
| 7,666,203 B2 | 2/2010 | Chanduszko et al. | |
| 7,762,940 B2 | 7/2010 | Henderson et al. | |
| 7,780,730 B2 | 8/2010 | Saidi | |
| 7,992,566 B2 | 8/2011 | Pflueger et al. | |
| 8,104,478 B2 | 1/2012 | Pflueger et al. | |
| 8,133,276 B2 | 3/2012 | Saidi | |
| 8,167,787 B2 | 5/2012 | Gillis | |
| 8,267,962 B2 | 9/2012 | Stupak | |
| 8,409,250 B2 | 4/2013 | Schmieding et al. | |
| 8,678,008 B2 | 3/2014 | Rousseau et al. | |
| 8,784,488 B2 | 7/2014 | Saidi | |
| 8,944,990 B2 | 2/2015 | Hamel et al. | |
| 9,480,594 B2 | 11/2016 | Saidi et al. | |
| 9,597,220 B2 | 3/2017 | Gonzales et al. | |
| 2002/0019670 A1 | 2/2002 | Crawley et al. | |
| 2002/0173848 A1 | 11/2002 | Sachs | |
| 2003/0028076 A1 | 2/2003 | Kuyava et al. | |
| 2003/0149447 A1 | 8/2003 | Morency et al. | |
| 2003/0199970 A1 | 10/2003 | Shanley | |
| 2004/0098098 A1 | 5/2004 | McGuckin et al. | |
| 2005/0004417 A1 | 1/2005 | Nelson et al. | |
| 2005/0142162 A1 | 6/2005 | Hunter et al. | |
| 2005/0154412 A1 | 7/2005 | Krueger et al. | |
| 2006/0085027 A1 | 4/2006 | Santin et al. | |
| 2006/0147492 A1 | 7/2006 | Hunter et al. | |
| 2006/0184224 A1 | 8/2006 | Angel | |
| 2006/0185680 A1 | 8/2006 | Bhat et al. | |
| 2006/0241650 A1 | 10/2006 | Weber et al. | |
| 2006/0276817 A1 | 12/2006 | Vassallo et al. | |
| 2007/0173848 A1 | 7/2007 | Lennox et al. | |
| 2007/0219575 A1 | 9/2007 | Mejia | |
| 2007/0250118 A1 | 10/2007 | Masini | |
| 2007/0277831 A1 | 12/2007 | Luhrs | |
| 2007/0293946 A1 | 12/2007 | Gonzales et al. | |
| 2008/0021495 A1 | 1/2008 | Lee et al. | |
| 2008/0027480 A1 | 1/2008 | Van Der Burg et al. | |
| 2008/0066794 A1 | 3/2008 | Durfee | |
| 2008/0097335 A1 | 4/2008 | Trogden et al. | |
| 2008/0167628 A1 | 7/2008 | Li et al. | |
| 2008/0208265 A1 | 8/2008 | Frazier et al. | |
| 2008/0234818 A1 | 9/2008 | Kang et al. | |
| 2008/0312688 A1 | 12/2008 | Nawrocki et al. | |
| 2009/0024133 A1 | 1/2009 | Keady et al. | |
| 2009/0024227 A1 | 1/2009 | Lesh | |
| 2009/0099577 A1 * | 4/2009 | Gonzales | A61B 17/064 606/143 |
| 2009/0198216 A1 | 8/2009 | Muni et al. | |
| 2009/0204130 A1 * | 8/2009 | Kantsevoy | A61B 17/0401 606/151 |
| 2009/0274743 A1 | 11/2009 | Edelman et al. | |
| 2009/0312791 A1 | 12/2009 | Lindh, Sr. et al. | |
| 2009/0318875 A1 | 12/2009 | Friedman | |

(56) References Cited

U.S. PATENT DOCUMENTS

| | | |
|---|---|---|
| 2010/0106255 A1 | 4/2010 | Dubin |
| 2010/0174138 A1 | 7/2010 | Chang et al. |
| 2010/0280611 A1 | 11/2010 | Saidi |
| 2011/0009872 A1 | 1/2011 | Mistry et al. |
| 2011/0264138 A1 | 10/2011 | Avelar et al. |
| 2013/0217958 A1 | 8/2013 | Mujwid et al. |
| 2013/0327333 A1 | 12/2013 | Ng et al. |
| 2015/0012090 A1 | 1/2015 | Saidi |
| 2016/0058556 A1 | 3/2016 | Rosenthal et al. |

FOREIGN PATENT DOCUMENTS

| | | |
|---|---|---|
| EP | 1475056 B1 | 10/2010 |
| EP | 1940320 B1 | 12/2010 |
| WO | WO00/76493 A1 | 12/2000 |
| WO | WO01/01957 A1 | 1/2001 |
| WO | WO01/19301 A1 | 3/2001 |
| WO | WO2002/076354 A1 | 10/2002 |
| WO | WO03/015664 A1 | 2/2003 |
| WO | WO2003/041612 A2 | 5/2003 |
| WO | WO2006/093533 A1 | 9/2006 |
| WO | WO2006/101610 A2 | 9/2006 |
| WO | WO2006/107957 A2 | 10/2006 |
| WO | WO2007/134215 A2 | 11/2007 |
| WO | WO2008/042058 A1 | 4/2008 |
| WO | WO2009/036290 A1 | 3/2009 |
| WO | WO2010/033682 A1 | 3/2010 |
| WO | WO2010/051273 A1 | 5/2010 |
| WO | WO2010/059586 A1 | 5/2010 |
| WO | WO2010/132648 A1 | 11/2010 |

OTHER PUBLICATIONS

Karen et al.; The use of percutaneous sutures for graft fixation in rhinoplasty; Archives Facial Plastic Surgery; 5(2); pp. 193-196; Mar.-Apr. 2003.

Lambert et al.; A new method for arterial drug delivery via removable stent (abstract); JACC; 21(2); p. 483A; Abstract No. 834-2; Feb. 1993.

Millman; Alar Batten grafting for management of collapsed nasal valve; Laryngoscope; 112(3); pp. 574-579; Mar. 2002.

Rhee et al.; Nasal valve surgery improves disease-specific quality of life; Laryngoscope; 115(3); pp. 437-440; Mar. 2005.

Westreich et al.; Defining nasal cartilage elasticity: Biomechanical testing of the tripod theory based on a cantilevered model; Arch Facial Plast Surg; 9(4); pp. 264-270; Jul./Aug. 2007.

Cole; Biophysics of nasal air flow: A review; American Journal of Rhinology; 14(4); pp. 245-249; Jul./Aug. 2000.

Cole; The four components of the nasal valve; American Journal of Rhinology; 17(2); pp. 107-110; Mar./Apr. 2003.

Fanous et al.; Collapsed nasal-valve widening by composite grafting to the nasal floor; Journal of Otolaryngology; 25(5); pp. 313-316; Oct. 1996.

Friedman et al.; Nasal Valve Suspension: An Improved, Simplified Technique for Nasal Valve Collapse; Laryngoscope; 113(2); pp. 381-385; Jan. 2003.

Baron et al.; U.S. Appl. No. 15/274,986 entitled "Nasal implants and systems and method of use," filed Sep. 23, 2016.

Saidi et al.; U.S. Appl. No. 15/339,220 entitled "Nasal implants and systems and methods of use," filed Oct. 31, 2016.

\* cited by examiner

APPARATUS AND METHODS FOR CORRECTING NASAL VALVE COLLAPSE

CROSS REFERENCE TO RELATED APPLICATIONS

This application is a continuation of U.S. patent application Ser. No. 13/129,846, filed Jun. 17, 2011, titled "APPARATUS AND METHODS FOR CORRECTING NASAL VALVE COLLAPSE", Publication No. US-2011-0251634-A1, which is a 35 U.S.C. § 371 national phase application of International Patent Application No. PCT/US2009/064689, filed Nov. 17, 2009, titled "APPARATUS AND METHODS FOR CORRECTING NASAL VALVE COLLAPSE", Publication No. WO 2010/059586, which claims priority to U.S. Provisional Patent Application No. 61/116,112, filed Nov. 19, 2008, titled "APPARATUS AND METHODS FOR CORRECTING NASAL VALVE COLLAPSE", the entire disclosure of which is specifically incorporated herein by reference.

FIELD OF THE INVENTION

The present disclosure relates generally to devices, systems and methods for correcting a nasal valve collapse and/or stabilizing lateral nasal cartilage.

BACKGROUND INFORMATION

Nasal valve collapse is a frequent and sufficient cause of nasal airway obstruction, characterized by a loss of support from lateral nasal cartilages typically observed following rhinoplasty, nasal trauma or in aged patients. Properly functioning nasal cartilage acts to keep the nasal passages open. If the lateral cartilages become weak, they collapse inward when a person inhales due to the negative pressure from the flow of air. This problem is currently largely untreated due to the complexity and highly variable results associated with current repair techniques, combined with the fact that a majority of patients are elderly or have a history of nasal surgery. These complex surgical procedures have been developed to correct valve collapse by reinforcing the lateral cartilages so adequate support can permit valve opening and thus eliminate the nasal airway obstruction.

However, many of these procedures require surgically opening the nose to replace structurally insufficient tissue with either synthetic or autologous tissue grafts. Results of these procedures have been highly variable and drawbacks include the lack of sufficient autologous grafting tissue, significant infection and extrusion of synthetic grafts, the potential for altering facial aesthetics and possible confounding effects on other nasal functionality. Another method for repairing nasal valve collapse, developed by Friedman et al., involves a bone-anchor suspension technique whereby a suture is anchored to the orbital rim and placed subcutaneously so as to loop through the upper lateral cartilage. Instead of imparting structural integrity to the collapsed cartilage, it applies tensile forces through this suture to prevent further collapse. Although the procedure has shown some promise, very few surgeons perform the technique because of the technical difficulties and potential complications. Complications occur because patients develop granulomas due to suture proximity to the nasal mucosa, which eventually necessitates implant removal.

Overall, nasal valve collapse is an oftentimes untreated problem due to inconsistent results from a myriad of very complex procedures performed by very few surgeons. As such, there remains a need for an endoscopic method to repair nasal valve in a simple, consistent manner.

SUMMARY

Exemplary embodiments of the present disclosure comprise a device configured for suspending a nasal valve. In certain embodiments, the device comprises a body portion comprising a proximal end, a distal end, and a plurality of barbs. The body portion can be configured to be inserted through or underneath the upper lateral cartilage of a patient and the plurality of barbs configured to engage the soft tissue overlying bony tissue proximal to the upper lateral cartilage. Certain embodiments may comprise a head portion coupled to the proximal end of the body portion, where the head portion is configured to engage the upper lateral cartilage of the patient when the plurality of barbs are engaged with the soft tissue overlying bony tissue proximal to the upper lateral cartilage.

In certain embodiments, the head portion is coupled to the body portion to form a "T" shape, while in other embodiments the head portion is coupled to the body portion to form an "L" shape or a hook shape. The plurality of barbs can be distributed along one side of the body portion and may be directed toward the proximal end of the body portion. In specific embodiments, the body portion and head portion are separated by an angle of between 90 and 120 degrees, more specifically between 95 and 115 degrees, and more specifically still between 100 and 110 degrees. In certain other embodiments, the body portion and head portion are separated by an angle of between 60 and 20 degrees, more specifically between 55 and 25 degrees, and more specifically still between 50 and 30 degrees.

Other embodiments comprise a method of stabilizing the upper lateral cartilage of a patient. The method may comprise: creating an aperture in the mucosa of the patient; inserting a device with a body portion and a head portion into the aperture, where the body portion of the device is inserted into the aperture prior to the head portion; advancing the device into the aperture so that the head portion engages the upper lateral cartilage of the patient; and engaging the plurality of barbs into soft tissue overlying the bony tissue proximal to the upper lateral cartilage. Specific embodiments may include engaging the plurality of barbs into soft tissue overlying the bony tissue lateral to the upper lateral cartilage, including, for example, the maxilla of the patient.

In certain embodiments, the body portion of the device pierces the upper lateral cartilage of the patient, and in other embodiments the body portion of the device is inserted between the upper lateral cartilage of the patient and bony tissue proximal to the upper lateral cartilage. In specific embodiments, the device is inserted into the aperture using a guiding needle sheath.

In certain embodiments, engaging the plurality of barbs into the soft tissue overlying the bony tissue proximal to the upper lateral cartilage of the patient comprises pressing down on an epidermal tissue proximal to the device. In specific embodiments, the soft tissue overlying the bony tissue is part of the orbital bone, while in other embodiments, the bony tissue is part of the nasal bone.

DETAILED DESCRIPTION OF EXEMPLARY EMBODIMENTS

Figure 1:
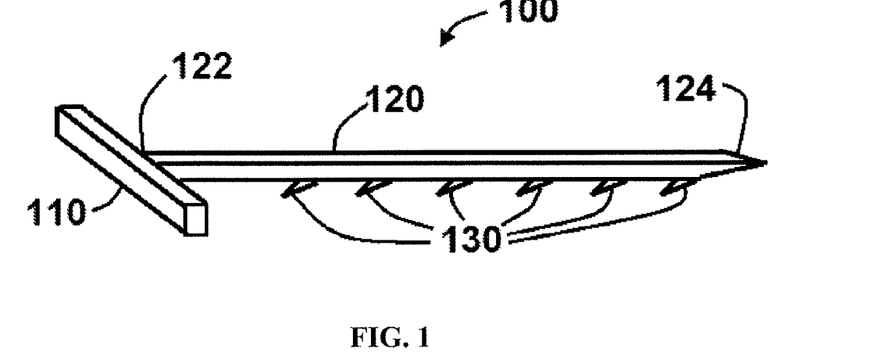
FIG. 1 illustrates a perspective view of a nasal valve suspension device according to an exemplary embodiment of the present disclosure.

Referring initially to the exemplary embodiment shown in FIG. 1, a nasal valve suspension device (NVSD) 100 is configured in a "T"-shape comprising a head portion 110 and a body portion 120 having a proximal end 122 and a distal end 124. A plurality of barbs 130 are disposed along body portion 120 so that the pointed ends of each barb are directed towards proximal end 122 (and head portion 110) and away from distal end 124. In certain embodiments, body portion 120 may be 0.5 to 3.0 cm in length, and head portion 110 may be approximately 0.5 centimeters in length.

In exemplary embodiments, intranasal endoscopic placement of NVSD 100 may be employed to allow NVSD 100 to support the nasal cartilage and prevent collapse of the nasal valve. In certain embodiments NVSD 100 may comprise a non-bioabsorbable material. In other embodiments, NVSD 100 may comprise a bioabsorbable material. Based on the material used to construct NVSD 100, the device can provide structural support while new tissue attachments are formed, and NVSD 100 may remain or degrade over time.

Figure 2:
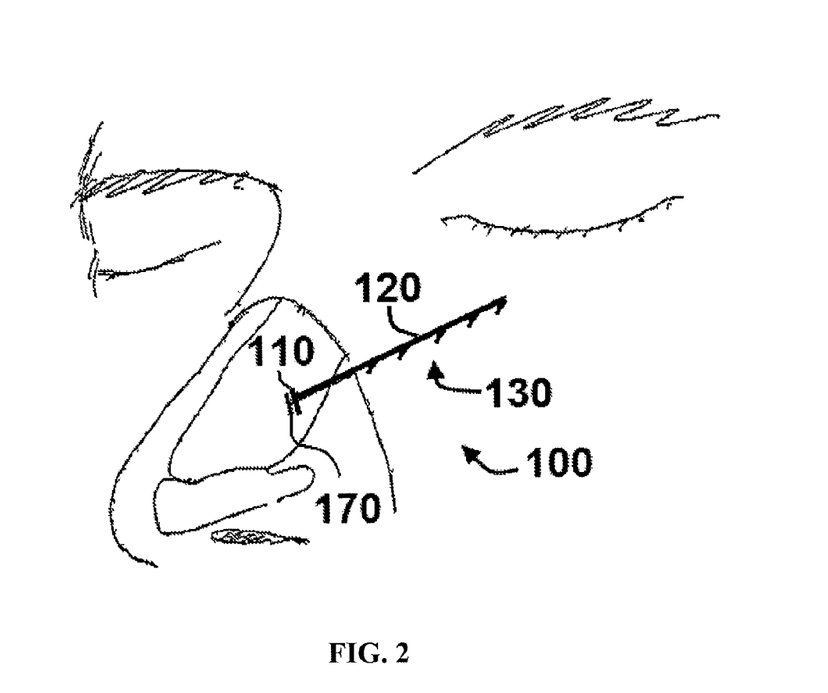
FIG. 2 illustrates a perspective view of the embodiment of FIG. 1 in an exemplary installed position.

Referring now to FIG. 2, NVSD 100 may be installed in an intranasal method by forming a slit or aperture 170 in the mucosa of a patient. Aperture 170 should be sized large enough to allow NVSD 100, including head portion 110, to pass through aperture 170. NVSD 100 can be inserted through aperture 170 so that body portion 120 is first inserted and head portion 110 follows. In this embodiment, NVSD 100 is oriented so that barbs 130 are facing down (e.g. towards the bone underlying the upper lateral cartilage and away from the epidermis). Body portion 120 can then be advanced to penetrate the upper lateral cartilage of the patient until head portion 110 engages the upper lateral cartilage. NVSD 100 can then be further advanced until head portion 110 exerts the desired amount of tension on the upper lateral cartilage.

When the desired amount of tension has been exerted on the upper lateral cartilage, the surgeon can press down on the epidermis above NVSD 100 so that barbs 130 engage the periosteum of the bone tissue lying lateral to the upper lateral cartilage (e.g., the orbital bone). When the surgeon releases the pressure exerted on NVSD 100, barbs 130 will remain engaged with the periosteum and will maintain the position of NVSD 100. Head portion 110 of NVSD 100 will continue to maintain a force exerted on the upper lateral cartilage and will stabilize the lateral cartilage (e.g., restrict the upper lateral cartilage from deflecting inwards) when the patient inhales.

Figure 3:
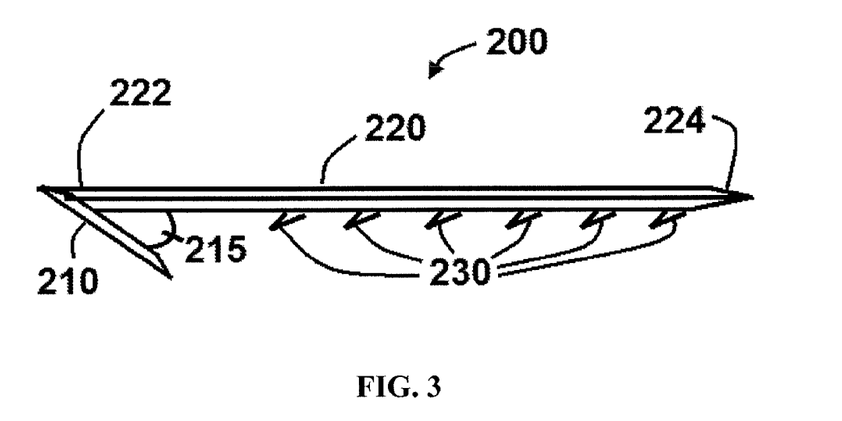
FIG. 3 illustrates a perspective view of a nasal valve suspension device according to an exemplary embodiment of the present disclosure.
Figure 4:
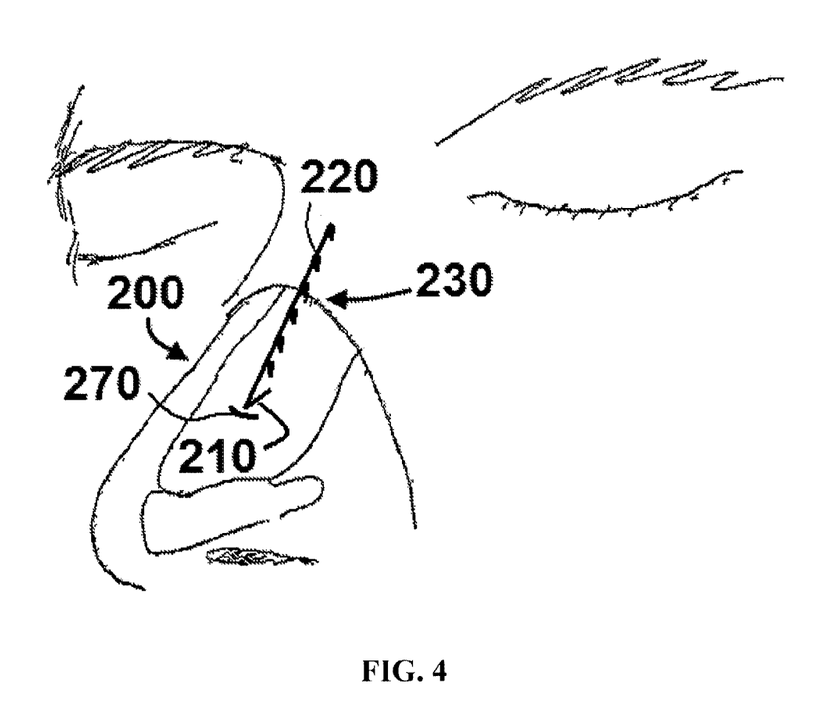
FIG. 4 illustrates a perspective view of the embodiment of FIG. 2 in an exemplary installed position.

Other embodiments of an NVSD may comprise a different configuration from that shown in FIGS. 1-2. Referring now to FIGS. 3-4, another exemplary embodiment of an NVSD is configured generally as a hook shape rather than the "T" shape of the previous embodiment. In the embodiment shown in FIGS. 3-4, NVSD 200 comprises a head portion 210 and a body portion 220 having a proximal end 222 and a distal end 224. Head portion 210 and body portion 220 are spaced apart from each other at an angle 215. In certain embodiments, angle 215 is between approximately 60 degrees and 20 degrees. In specific embodiments, angle 215 is between 55 degrees and 25 degrees, and in more specific embodiments angle 215 is between 50 and 40 degrees. A plurality of barbs 230 are disposed along body portion 220 so that the pointed ends of each barb are directed towards proximal end 222 (and head portion 210) and away from distal end 224.

As shown in FIG. 4, this embodiment can be installed through a mucosal aperture 270 so that NVSD 200 either penetrates or is placed above the superior aspect of the upper lateral cartilage. NVSD 200 can be installed so that body portion 220 is inserted first and barbs 230 are facing towards the bony tissue of the nasal bone. The surgeon can advance NVSD 200 so that head portion 210 engages the upper lateral cartilage. When the desired amount of tension has been placed on the upper lateral cartilage, the surgeon can press down on the epidermis above NVSD 200 so that barbs 230 engage the periosteum of the bone tissue below. Both NVSD 200 and NVSD 300 may be installed in either of the positions shown in FIGS. 2 and 4.

Figure 5:
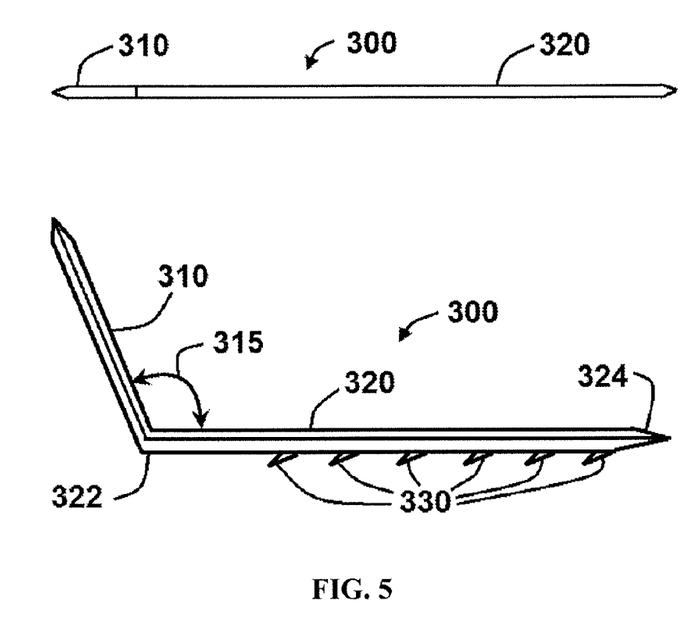
FIG. 5 illustrates side and top views of a nasal valve suspension device according to an exemplary embodiment of the present disclosure.

Referring now to FIG. 5, another exemplary embodiment of an NVSD is similar to that shown in FIG. 3, but comprises generally an "L" shape (when viewed from the side), rather than a "hook" shape. In the embodiment shown in FIG. 5, NVSD 300 comprises a head portion 310, a body portion 320 having a proximal end 322 and a distal end 324. Head portion 310 and body portion 320 are spaced apart from each other at an angle 315. In certain embodiments, angle 315 is between approximately 90 degrees and 120 degrees. In specific embodiments, angle 315 is between 95 degrees and 115 degrees, and in more specific embodiments angle 315 is between 100 and 110 degrees. A plurality of barbs 330 are disposed along body portion 320 so that the pointed ends of each barb are directed towards proximal end 322 (and head portion 310) and away from distal end 324.

Figure 6:
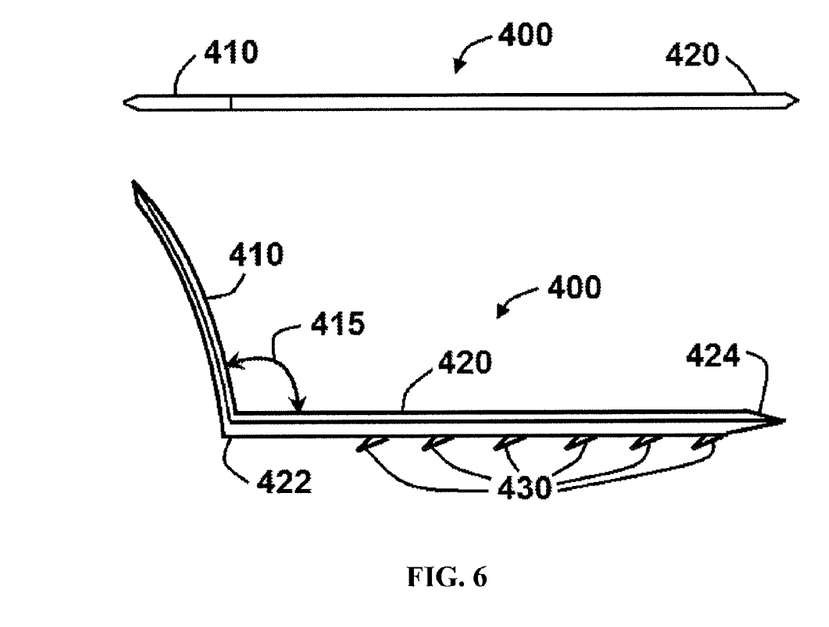
FIG. 6 illustrates side and top views of a nasal valve suspension device according to an exemplary embodiment of the present disclosure.

Referring now to FIG. 6, another exemplary embodiment of an NVSD is similar to that shown in FIG. 5, but comprises a head portion 410 that is slightly curved. NVSD 400 comprises head portion 410, a body portion 420 having a proximal end 422 and a distal end 424. Head portion 410 and body portion 420 are spaced apart from each other at an angle 415. A plurality of barbs 430 are disposed along body portion 420 so that the pointed ends of each barb are directed towards proximal end 422 (and head portion 410) and away from distal end 424. The embodiment in FIG. 6 can be installed in the same manner as the embodiment of FIG. 5, described below.

Figure 7:
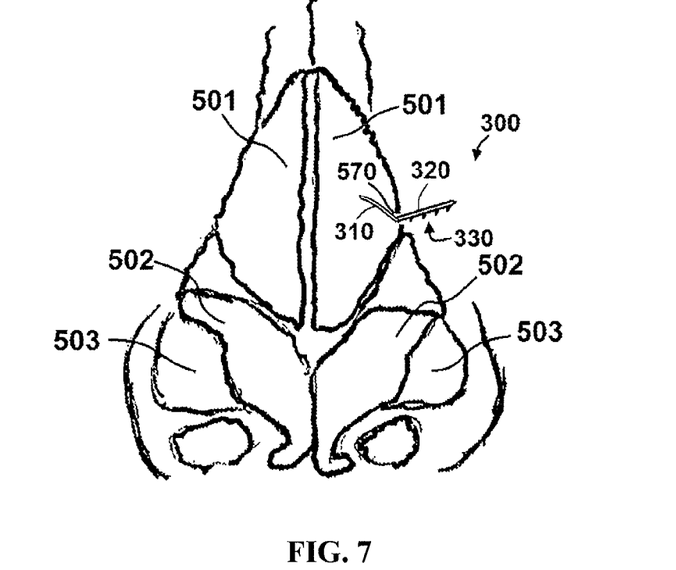
FIG. 7 illustrates a front view of the embodiment of FIG. 5 in an exemplary installed position.
Figure 8:
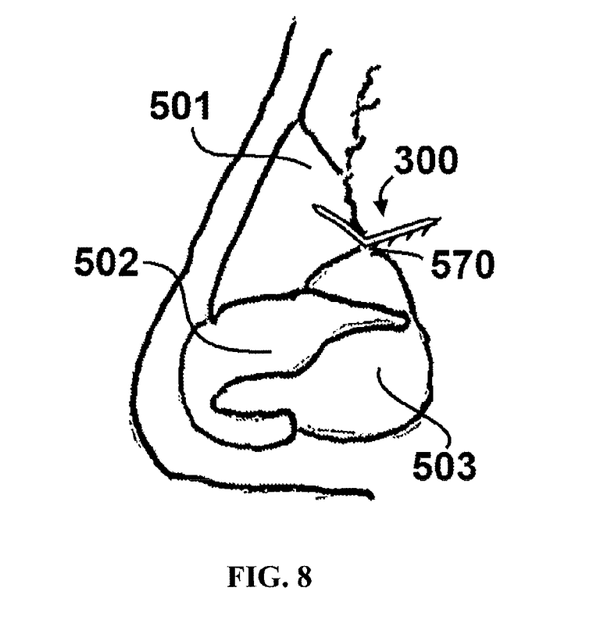
FIG. 8 illustrates a side view of the embodiment of FIG. 5 in an exemplary installed position.

As shown in FIGS. 7 and 8, NVSD 300 can be installed so that body portion 320 is installed through an aperture 570 in upper lateral cartilage 501. Also visible in FIGS. 7 and 8 are lower lateral cartilage 502 and accessory cartilage 503. Head portion 310, however, does not extend through aperture 570, but instead remains under upper lateral cartilage 501. Body portion 320 is inserted through aperture 570 sufficiently for head portion 310 to engage upper cartilage 501. During installation, body portion 320 is oriented so that barbs 330 are facing towards the bone tissue proximal to body portion 320. Similar to previous embodiments, the surgeon can press down on the epidermis above NVSD 300 so that barbs 330 engage the periosteum of the bone tissue lying lateral to the upper lateral cartilage 501 (e.g., the orbital bone).

When the surgeon releases the pressure exerted on NVSD 300, barbs 330 will remain engaged with the periosteum and will maintain the position of NVSD 300. Head portion 310 of NVSD 300 will continue to maintain a force exerted on upper lateral cartilage 501 and will restrict upper lateral cartilage 501 from deflecting inwards when the patient inhales. Angle 315 between head portion 310 and body portion 320 is configured so that head portion 310 maintains a sufficient force on upper lateral cartilage 501 to restrict deflection during inhalation.

As demonstrated in the above-described devices and methods, exemplary embodiments of this disclosure can be implemented to support nasal cartilage and keep the nasal passages open, particularly during inhalation. Exemplary embodiments utilize barbs that engage the periosteum of bone tissue proximal to the nasal cartilage and serve to maintain the device in the desired position. Exemplary devices also comprise a portion that engages the nasal cartilage and exerts a force against it that resists the collapse of the cartilage.

EQUIVALENTS AND SCOPE

While an exemplary embodiment is described herein, it will be understood that various modifications to the method and apparatus can be made without departing from the scope of the present invention. For example, the positions of the control mechanisms may be varied from those illustrated. Furthermore, the sequential recitation of steps in any claim is not a requirement that the steps be performed in any particular order, unless otherwise so stated.

The foregoing has been a description of certain non-limiting preferred embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims. For example, the positions of the control mechanisms may be varied from those illustrated.

In the claims articles such as "a", "an", and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that embodiments of the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. In addition, embodiments of the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention can be excluded from any one or more claims. For purposes of brevity, all of the embodiments in which one or more elements, features, purposes, or aspects is excluded are not set forth explicitly herein.

The following references are herein incorporated by reference:
  U.S. Pat. No. 4,461,281
  U.S. Pat. No. 5,131,382
  U.S. Pat. No. 5,531,744
  U.S. Pat. No. 5,749,893
  U.S. Pat. No. 5,785,647
  U.S. Pat. No. 5,897,523

U.S. Pat. No. 6,010,054
U.S. Pat. No. 6,183,433
U.S. Pat. No. 6,656,195

What is claimed is:

1. A device configured for suspending a nasal valve, the device comprising:
   a body portion comprising a proximal end, a distal end, and a plurality of barbs disposed along only a first side of the body portion such that a second side of the body portion opposite the first side does not include the plurality of barbs, wherein the body portion is configured to be inserted through or underneath an upper lateral cartilage of a patient, and wherein the plurality of barbs are configured to engage a soft tissue overlying a bony tissue proximal to the upper lateral cartilage; and
   a head portion coupled to the proximal end of the body portion, wherein the head portion is an entirety of the device that is proximal of the proximal end of the body portion, wherein the head portion is biased to engage the upper lateral cartilage of the patient to exert a tension force against the upper lateral cartilage when the plurality of barbs are engaged with the soft tissue overlying the bony tissue proximal to the upper lateral cartilage, and wherein, in a direction from the second side of the body portion to the first side of the body portion, the head portion does not extend past the first side of the body portion such that each of the plurality of barbs extend farther away from the first side of the body portion than any part of the head portion,
   wherein the plurality of barbs, in response to applied pressure on epidermal tissue proximate the device, engage a periosteum of a bony tissue lying lateral to the upper lateral cartilage such that the second side of the body portion does not engage the soft tissue, and
   wherein the head portion maintains the tension force against the upper lateral cartilage and resists inward deflection of the upper lateral cartilage during inhalation.

2. The device of claim 1, wherein the head portion is coupled to the body portion to form a "T" shape.

3. The device of claim 1, wherein the head portion is coupled to the body portion to form an "L" shape.

4. The device of claim 1, wherein the head portion is coupled to the body portion to form a hook shape.

5. The device of claim 1, wherein the plurality of barbs are directed toward the proximal end of the body portion.

6. The device of claim 1, wherein the body portion and head portion are separated by an angle of between 90 and 120 degrees.

7. The device of claim 1, wherein the body portion and head portion are separated by an angle of between 100 and 110 degrees.

8. The device of claim 1, wherein the body portion and head portion are separated by an angle of between 60 and 20 degrees.

9. The device of claim 1, wherein the body portion and head portion are separated by an angle of between 50 and 30 degrees.

10. The device of claim 1, wherein the device is configured to be inserted through an aperture in a mucosa of the patient.

11. The device of claim 1, wherein the device is configured to be inserted through an aperture in the upper lateral cartilage of the patient.

12. The device of claim 1, wherein the body portion has a length of 0.5 cm to 3.0 cm.

13. The device of claim 1, wherein the head portion has a length of 0.5 CM.

14. The device of claim 1, wherein the device comprises a non-bioabsorbable material.

15. The device of claim 1, wherein the device comprises a bioabsorbable material.

16. The device of claim 15, wherein the device comprises a non-bioabsorbable material.

17. The device of claim 1, wherein the head portion includes a curved shape.

18. The device of claim 1, wherein the head portion includes a straight shape.

* * * * *